United States Patent [19]

Shiokawa et al.

[11] Patent Number: 4,559,079
[45] Date of Patent: Dec. 17, 1985

[54] SUBSTITUTED PHENYLSULFONYL GUANIDINE HERBICIDES AND INTERMEDITATES THEREFOR

[75] Inventors: Kozo Shiokawa, Kanagawa; Koichi Moriya, Tokyo; Toshio Goto, Kanagawa; Atsumi Kamochi; Shigeo Kohama, both of Tokyo, all of Japan

[73] Assignee: Nihon Tokushu Noyaku Seizo K.K., Tokyo, Japan

[21] Appl. No.: 636,521

[22] Filed: Aug. 1, 1984

[30] Foreign Application Priority Data

Aug. 10, 1983 [JP] Japan .................................. 58-145157

[51] Int. Cl.[4] .................. C07D 239/42; C07D 239/47; A01N 47/36
[52] U.S. Cl. ....................... 71/92; 544/321; 544/332
[58] Field of Search ...................... 544/321, 332; 71/92

[56] References Cited

U.S. PATENT DOCUMENTS 4,378,991 4/1983 Levitt ....................................... 71/93

FOREIGN PATENT DOCUMENTS 0005986 12/1979 European Pat. Off. .
0023422 2/1981 European Pat. Off. .
0043642 1/1982 European Pat. Off. .
0056969 8/1982 European Pat. Off. .
0074595 3/1983 European Pat. Off. .
117014 8/1984 European Pat. Off. .................. 71/92
3334455 9/1984 Fed. Rep. of Germany .......... 71/92

Primary Examiner—Robert Gerstl
Attorney, Agent, or Firm—Sprung Horn Kramer & Woods

[57] ABSTRACT

Substituted phenylsulfonyl guanidines of the formula

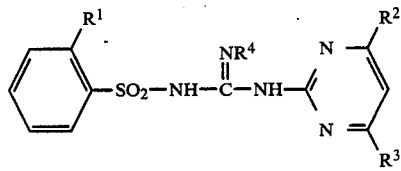

in which
$R^1$ is a phenyl or phenoxy group,
$R^2$ and $R^3$ each independently is a lower alkyl or lower alkoxy group, and
$R^4$ is a hydrogen atom, a lower alkyl group or a lower alkoxy group, which possess herbicidal activity. Intermediates therefor of the formulas

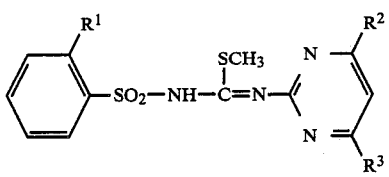

and

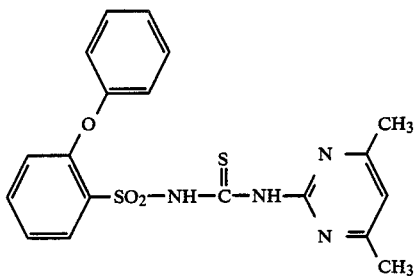

are new and also herbicidal. Intermediates of the formulas

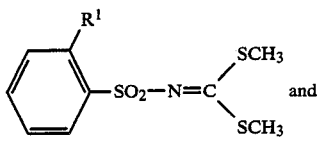

and

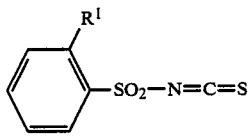

are also new.

9 Claims, No Drawings

SUBSTITUTED PHENYLSULFONYL GUANIDINE HERBICIDES AND INTERMEDIATES THEREFOR

DETAILED DESCRIPTION OF THE INVENTION

This invention relates to novel substituted phenylsulfonyl guanidine derivatives, intermediates therefor, processes for their production and their use in controlling weeds.

More specifically, this invention relates to substituted phenylsulfonyl guanidine derivatives represented by the following formula (I).

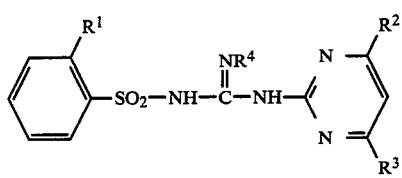
(I)

wherein $R^1$ represents a phenyl or phenoxy group, each of $R^2$ and $R^3$ represents a lower alkyl or lower alkoxy group, and $R^4$ represents a hydrogen atom, a lower alkyl group or a lower alkoxy group.

The compounds of the invention represented by general formula (I) can be produced, for example, by the following process (i) to which the invention also pertains.

Process (i)

A process for producing the substituted phenylsulfonyl guanidine derivatives of general formula (I), which comprises reacting a compound represented by the general formula

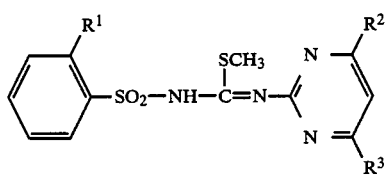
(II)

wherein $R^1$, $R^2$ and $R^3$ are as defined above, with a compound of the general formula $$R^4-NH_2 \quad (III)$$

wherein $R^4$ is as defined above.

This invention also relates to substituted phenylsulfonyl isothiourea derivatives of general formula (II) which are intermediates in the process (i) above, and also to the following processes (ii) and (iii) for producing the compounds (II).

Process (ii)

A process for producing the substituted phenylsulfonyl isothiourea derivatives of general formula (II), which comprises reacting a compound of the general formula

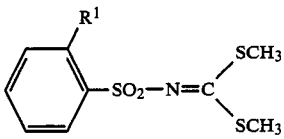
(IV)

wherein $R^1$ is as defined above, with a compound of the general formula

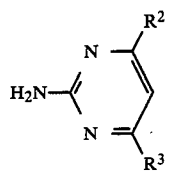
(V)

wherein $R^2$ and $R^3$ are as defined above.

Process (iii)

A process for producing the substituted phenylsulfonyl isothiourea derivatives of general formula (II), which comprises reacting a compound of the general formula

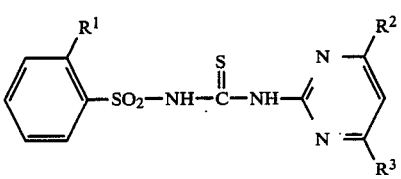
(VI)

wherein $R^1$, $R^2$ and $R^3$ are as defined, with a methylating agent in the presence of a base.

This invention also relates to substituted phenylsulfonyl thiourea derivatives of general formula (VI) which are intermediates in the process (iii) and the following process (iv) for producing the derivatives of formula (VI).

Process (iv)

A process for producing the substituted phenylsulfonyl thiourea derivatives of general formula (VI), which comprises reacting a compound of the general formula

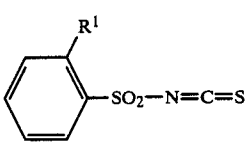
(VII)

wherein $R^1$ is as defined above, with the compound of general formula (V) given above.

This invention also relates to a weed controlling agent comprising the substituted phenylsulfonyl guanidine derivative of general formula (I) as an active ingredient.

The present inventors have extensively worked in order to obtain novel compounds having excellent herbicidal activity, and have now succeeded in synthesizing the substituted phenylsulfonyl guanidine derivatives of general formula (I). They have found that these compounds are new compounds not described in the prior literature, and have excellent weed controlling activity. It has also been found that when these compounds are used as weed controlling agents for aquatic paddies, they show an outstanding selective weed controlling effect against paddy weeds without causing phytotoxicity to rice plants.

The compounds of general formula (I) in accordance with this invention are quite novel compounds not described in the prior literature. They are structurally characterized by the fact that they are based on the guanidine skeleton and have a 2-biphenylylsulfonyl group or 2-phenoxyphenylsulfonyl group bonded to the N atom at the 1-position, a substituted-pyrimidin-2-yl group bonded to the N atom at the 2-position, and a hydrogen atom or a lower alkyl or alkoxy group bonded to the N atom at the 3-position. It has been found that by dint of the aforesaid unique chemical structure, these compounds exhibit the above excellent biological characteristics.

The compounds of general formula (II), (IV), (VI), and (VII), which are intermediates for the production of the substituted phenylsulfonyl guanidine derivatives of general formula (I), are also quite novel compounds not described in the prior literature. Among these intermediates, the substituted phenylsulfonyl isothiourea derivatives of general formula (II) and the substituted phenylsulfonyl thiourea derivatives of general formula (VI) have excellent weed controlling activity by themselves, and are useful not only as intermediates for production of other useful compounds but also as weed controllers.

It is an object of this invention therefore to provide substituted phenylsulfonyl guanidine derivatives of general formula (I), intermediates thereof, processes for production thereof, and use thereof as weed controlling agents, particularly as selective weed controlling agents against aquatic paddy weeds.

The above and other objects and advantages of this invention will become more apparent form the following description.

The compounds of this invention show an outstanding selective control effect when used as a pre-emergence soil treating agent or a stalk foliar/soil treating agent against aquatic paddy weeds.

The compounds of this invention have high safety, outstanding weed controlling activity and a broad herbicidal spectrum.

For example, they are characterized by having weed controlling activity against the following aquatic paddy weeds without any phytotoxicity to rice:

| Plant name | Latin scientific name |
| --- | --- |
| Dicotyledons | |
| Kikashigusa | *Rotala indica* Koehne |
| False pimpernel | *Lindernia produmbens* Philcox |
| False loosestrife | *Ludwigia prostrata* Roxburgh |
| Largeleaf pondweed | *Potamogeton distinctus* A. Bennett |
| American waterwort | *Elatine triandra* Schkuhr |
| Monocotyledons | |
| Barnyard grass | *Echinochloa crus-galli* Beauv. var *oryzicola* Ohwi |
| Monochoria | *Monochoria vaginalis* Presl |
| Spikerush | *Eleocharis acicularis* Roem. et Schult. |
| Water chestnut | *Eleocharis Kuroguwai* Ohwi |
| Umbrella plant | *Cyperus difformis* L. |
| Mizugayatsuri | *Cyperus serotinus* Rottboel |
| Urikawa | *Sagittaria pygmaea* Miq. |
| Narrowleaf waterplantain | *Alisma canaliculatum* A. Br. et Bouche |

| Plant name | Latin scientific name |
| --- | --- |
| Bulrush | *Scirpus juncoides* Roxburgh var. |

Furthermore, they are characterized by having weed controlling activity against the following upland farm weeds:

| Plant name | Latin scientific name |
| --- | --- |
| Dicotyledons | |
| Tade | Polygonum sp. |
| Goosefoot | *Chenopodium album* L. var. *centrorubrum* Makino |
| Common chickweed | *Stellaria media* Villars |
| Common purslane | *Portulaca oleracea* Linnaeus |
| Monocotyledons | |
| Barnyard grass | *Echinochloa crus-galli* P. Beauv. |
| Fingergrass | *Digitaria adscendens* Henr. |
| Chufa | *Cyperus microiria* Steud. |

They are further characterized by causing no phytotoxicity to such upland farm crops as mustard, cotton, carrots, beans, potato, beets and cabbage (dicotyledons); and corn, rice, oats, barley, wheat, *Panicum milliaceum* and *Saccharum offcinarum* (monocotyledons).

It should be understood that the plant's names given above are typical examples of each of the general Latin scientific names.

The applicability of the active compounds of this invention is not limited to weeds in aquatic paddies and upland farms. They are also effective against weeds noxious to mat rush (*Juncus effusus* Linnaeus var. *decipiens* Buchanan), weeds occurring in lands which are temporarily out of cultivation, etc. The term "weeds", as used herein, means all plants which occur in undesired sites in the broadest sense.

The substituted phenylsulfonyl guanidine derivatives of this invention represented by general formula (I) can be synthesized, for example, by the following process (i):

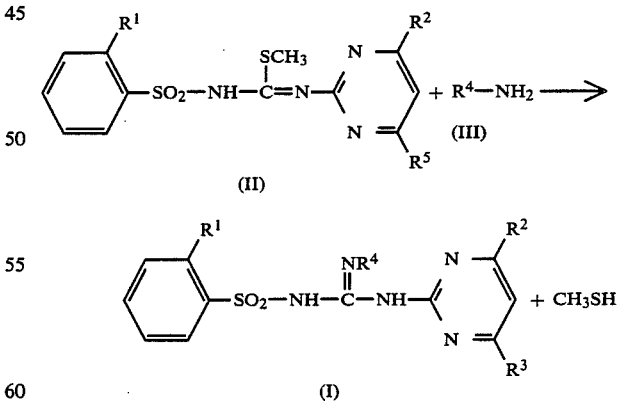

In the formulae, $R^1$, $R^2$, $R^3$ and $R^4$ are as defined above.

In the above reaction scheme:
$R^1$ represents a phenyl or phenoxy group;
each of $R^2$ and $R^3$ represents a lower alkyl group or a lower alkoxy group, specifically such lower alkyl groups as methyl, ethyl, propyl, isopropyl, and n-(iso-, sec-, or tert-)butyl, and lower alkoxy groups having the same lower alkyl groups as above; and R⁴ represents a hydrogen atom, a lower alkyl group, or a lower alkoxy group, specific examples of the lower alkyl and lower alkoxy groups being the same as given above with regard to R² and R³.

In the process for producing the substituted phenylsulfonyl guanidine derivatives of general formula (I) shown by the above reaction scheme, specific examples of the starting compound of general formula (II) include:

1-(2-biphenylylsulfonyl)3-(4-methoxy-6-methyl-pyrimidin-2-yl)2-methylisothiourea, 1-(2-biphenylylsulfonyl)3-(4,6-dimethylpyrimidin-2-yl)2-methylisothiourea, and 3-(4,6-dimethylpyrimidin-2-yl)2-methyl-1-(2-phenoxyphenylsulfonyl)isothiourea.

Likewise, specific examples of the starting compound of general formula (III) are ammonia, O-methylhydroxylamine, methylamine and O-propylhydroxylamine.

The above process is specifically illustrated by the following typical example:

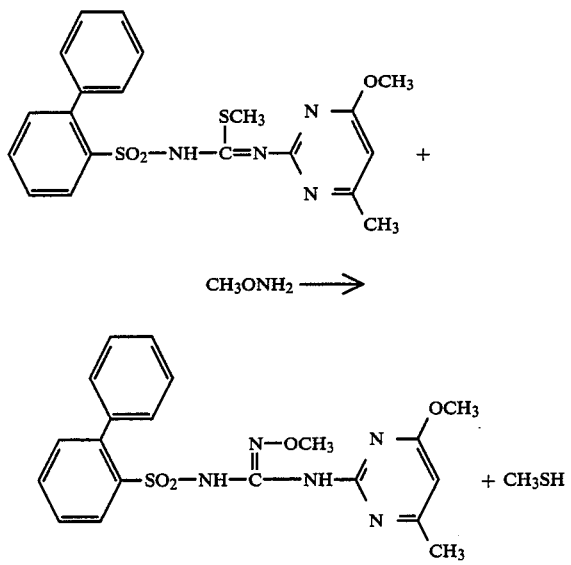

The above process for producing the compound of this invention can be carried out, desirably in a solvent or diluent. For this purpose, all inert solvents and diluents can be used.

Examples of such solvents or diluents include aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, di-isopropyl ether, dibutyl ether, propyelene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; esters such as ethyl acetate and amyl acetate; acid amides such as dimethylformamide and dimethylacetamide; sulfones and sulfoxides such as dimethyl sulfoxide and sulfolane; and organic bases such as pyridine.

The above process of this invention can be carried out over a broad temperature range, generally at a temperature between −20° C. and the boiling point of the mixture, desirably at a temperature between about 0° C. and about 100° C. Desirably, the reaction is carried out under atmospheric pressure, but it is also possible to operate under elevated or reduced pressures.

The substituted phenylsulfonyl isothiourea derivative of general formula (II) which is an intermediate can be produced, for example, by the following process (ii) or (iii).

Process (ii)

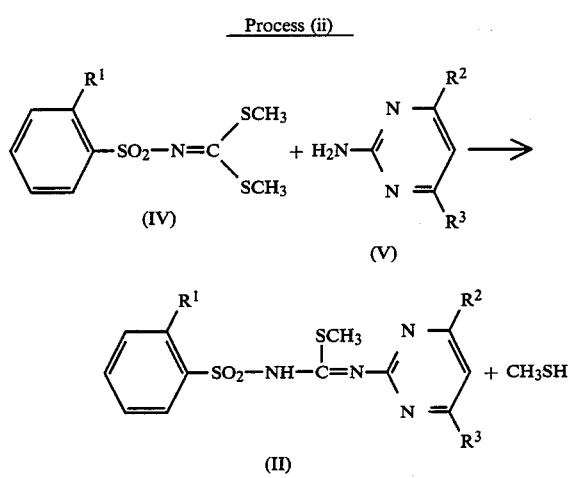

In the formulae, R¹, R² and R³ are as defined hereinabove.

In the process for producing the substituted phenylsulfonyl isothiourea derivative of general formula (II) shown by the above reaction scheme, specific examples of the starting compound of general formula (IV) are dimethyl N-(2-biphenylylsulfonyl)carbonimidodithioate, and dimethyl N-(2-phenoxyphenylsulfonyl)carbonimidodithioate.

Likewise, specific examples of the starting compound of general formula (V) are 2-amino-4,6-dimethylpyrimidine, and 2-amino-4-methoxy-6-methylpyrimidine.

The above process is specifically illustrated by the following typical example

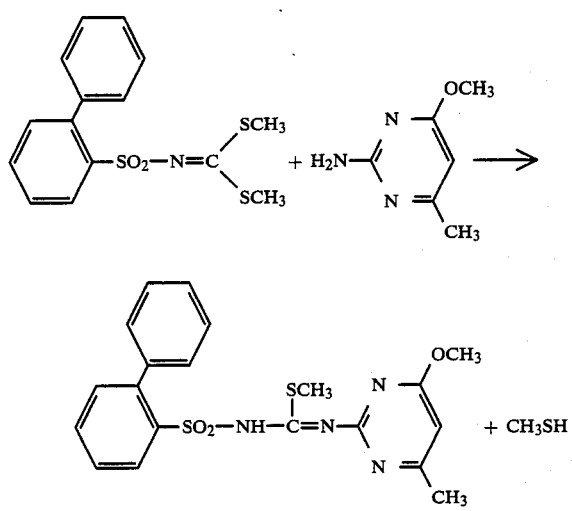

By performing the above process preferably using the same inert solvent or diluent as above, the desired product of high purity can be obtained in a high yield.

The above process can also be carried out efficiently in the presence of, for example, sodium hydride or potassium hydride.

The above reaction can be performed over a wide temperature range, for example, at a temperature between about −20° C. to the boiling point of the mixture, preferably between about 0° and about 100° C. Preferably, the reaction is carried out under atmospheric pressure, but it is also possible to operate under elevated or reduced pressures.

Process (iii)

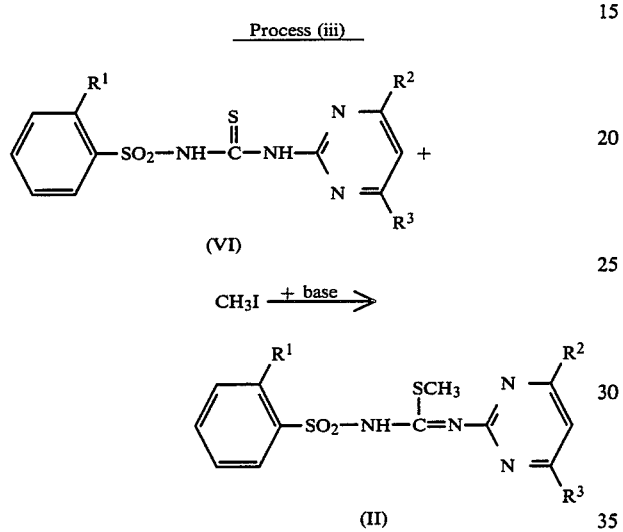

In the formulae, $R^1$, $R^2$ and $R^3$ are as defined above.

In the process for producing the substituted phenylsulfonyl isothiourea derivatives of general formula (II) shown by the above reaction scheme, specific examples of the starting compound of general formula (VI) include:

1-(2-biphenylylsulfonyl)3-(4-methoxy-6-methyl-pyrimidin-2-yl)thiourea,
1-(2-biphenylylsulfonyl)3-(4,6-dimethylpyrimidin-2-yl)thiourea, and
3-(4,6-dimethylpyrimidin-2-yl)1-(2-phenoxyphenyl-sulfonyl)thiourea.

Examples of the methylating agent are methyl iodide, dimethyl sulfate, methyl bromide and methyl chloride.

The above process should be carried out in the presence of a base. Examples of the base are metallic sodium, metallic potassium, metallic lithium, sodium hydroxide, potassium hydroxide and lithium hydroxide.

The above process is illustrated specifically by the following typical example:

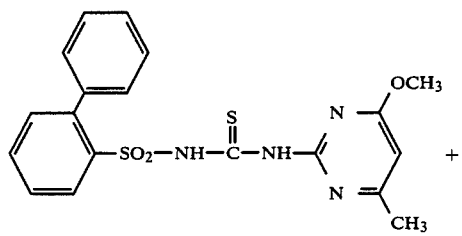

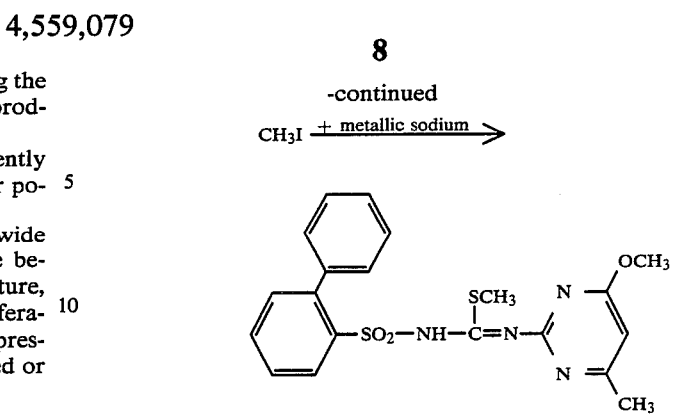

The above process is carried out preferably by using the same inert solvent or diluent as described hereinabove to give the desired product of high purity in a high yield.

The above reaction can be carried out over a wide temperature range, for example, at a temperature between about −20° C. and the boiling point of the mixture, preferably between about 0 and about 100° C. Preferably, the reaction is carried out under atmospheric pressure, but it is also possible to operate under elevated or reduced pressure.

The substituted phenyl sulfonyl thiourea derivatives of general formula (VI) which are intermediates can be synthesized, for example, by the following process (iv):

Process (iv)

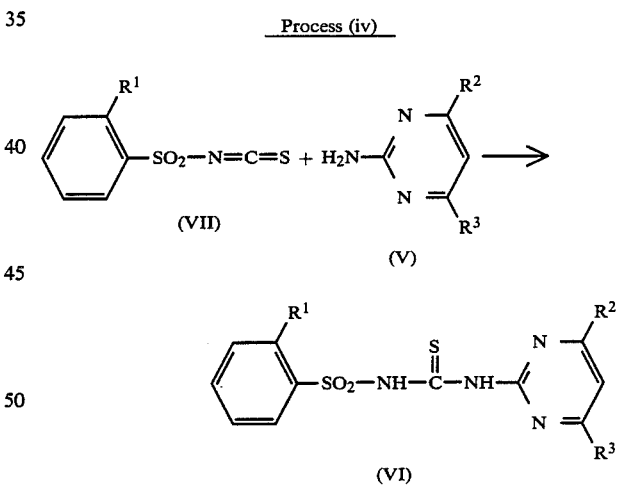

In the formulae, $R^1$, $R^2$ and $R^3$ are as defined above.

In the process for producing the substituted phenylsulfonyl thiourea derivatives of general formula (VI) shown by the above reaction scheme, specific examples of the starting compound of general formula (VII) are 2-phenylbenzenesulfonyl isothiocyanate and 2-phenoxybenzenesulfonyl isothiocyanate.

Specific examples of the starting compound of general formula (V) may be the same as those given with regard to process (ii).

The above process is illustrated specifically by the following typical example:

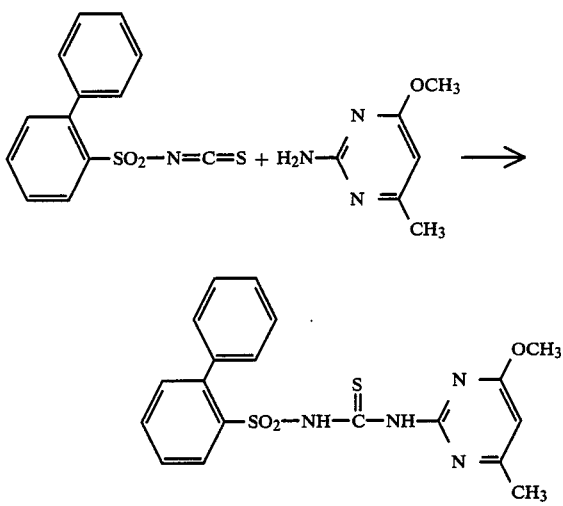

The above process is performed preferably by using the same inert solvent or diluent as described hereinabove to give the desired product of high purity in a high yield.

The above reaction can be carried out over a wide temperature range, for example at a temperature between about −20° C. and the boiling point of the mixture, preferably between about 0° to about 100° C. The reaction is carried out preferably under atmospheric pressure, but it is also possible to operate under reduced or elevated pressures.

The reaction can be promoted by using an organic base such as triethylamine and diazabicyclooctane as a catalyst.

For use as a weed controlling agent, the compound of this invention represented by general formula (I) may be used as such after diluting it directly with water, or after formulating it into various forms using agriculturally acceptable adjuvants by methods generally practiced in the production of agricultural chemicals. In actual use, these compositions in various forms are applied either directly or after diluting them with water to the desired concentrations. Examples of the agriculturally acceptable adjuvants, as referred to herein, are diluents (solvents, extenders, carriers), surface-active agents (solubilizing agents, emulsifiers, dispersants, wetting agents), stabilizers, stickers, aerosol propellants, and synergists.

Examples of the solvents are water, and organic solvents, for example hydrocarbons (e.g., n-hexane, petroleum ether, naphtha, petroleum fractions (e.g., paraffin waxes, kerosen, light oils, middle oils, heavy oils), benzene, toluene, and xylenes), halogenated hydrocarbons (e.g., methylene chloride, carbon tetrachloride, trichloroethylene, ethylene chloride, ethylene dichloride, chlorobenzene and chloroform), alcohols (e.g., methyl alcohol, ethyl alcohol, propyl alcohol, and ethylene glycol), ethers (e.g., ethyl ether, ethylene oxide and dioxane), alcohol ethers (e.g., ethylene glycol monomethyl ether), ketones (e.g., acetone and isophorone), esters (e.g., ethylene acetate and amyl acetate), amides (e.g., dimethylformamide and dimethylacetamide) and sulfoxides (e.g., dimethyl sulfoxide).

Examples of the extenders or carriers include inorganic powders, for example sulfur, slaked lime, magnesium lime, gypsum, calcium carbonate, silica, perlite, pumice, calcite, diatomaceous earth, amorphous silica, alumina, zeolites, and clay minerals (e.g., pyrophyllite, talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfuric acid esters (e.g., sodium laurylsulfate), arylsulfonic acid salts (e.g., alkylarylsulfonic acid salts and sodium alkylnaphthalenesulfonates), succinic acid salts and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chloride) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers; stickers (e.g., agricultural soaps, casein lime, sodium alginate, polyvinyl alcohol, vinyl acetate-type adhesives and acrylic adhesives); effect-prolonging agents; dispersion stabilizers (e.g., casein, tragacanth, carboxymethyl cellulose and polyvinyl alcohol); and synergists.

The compounds of this invention can be formulated into various forms by methods generally practiced in the field of manufacturing agricultural chemicals. Examples of the forms include emulsifiable concentrates, oils, wettable powders, soluble powders, suspensions, dusts, granules, pulverulent preparations and capsules.

The weed controlling agent of this invention may contain about 0.001 to about 100% by weight, preferably about 0.005 to about 95% by weight, of the aforesaid active ingredient.

In actual use, the suitable amount of the active compound in the aforesaid preparations in various forms and ready-to-use preparations is, for example, about 0.01 to about 95% by weight, preferably about 0.05 to about 60% by weight.

The content of the active ingredient can be properly varied depending upon the form of the preparation, the method, purpose, time and locus of its application, the state of occurrence of weeds, etc.

If required, the compound of this invention may be used further in combination with other agricultural chemicals, for example insecticides, fungicides, miticides, nematocides, antiviral agents, herbicides, plant growth regulators and attractants (e.g., organophosphorus ester compounds, carbamate compounds, dithio (or thiol) carbamate compounds, organic chlorine compounds, dinitro compounds, organic sulfur or metal compounds, antibiotics, substituted diphenyl ether compounds, urea compounds, and triazine compounds), and/or fertilizers.

Various compositions and ready-to-use preparations containing the aforesaid active ingredient of the invention can be applied by various methods generally practiced in the field of agricultural chemical application, for example spraying (liquid spraying, misting, atomizing, dust scattering, granule scattering, water surface application and pouring); and soil application (mixing with the soil, and sprinkling). They can also be used by the so-called ultralow volume spraying method. According to this method, the active ingredient may be included in an amount of 100%.

The rate of application per unit area is, for example, about 0.1 to about 3.0 kg, preferably about 0.2 to about 1 kg, per hectare. In special cases, however, it may, and sometimes should, be outside the specified range.

According to this invention, there is provided a weed controlling composition comprising the compound of general formula (I), (II) and (VI) as an active ingredient and a diluent (a solvent and/or an extender and/or a carrier) and/or a surface-active agent, and if further required, a stabilizer, s sticker, a synergist, etc.

The invention also provides a method for controlling weeds, which comprises applying to weeds and/or their habitat the compound of general formula (I), (II) or (VI) alone or in admixture with a diluent (a solvent and/or an extender and/or a carrier) and/or a surface active agent and if required, a stabilizer, a sticker, a synergist, etc.

The following examples illustrate the present invention specifically. It should be noted however that the invention is not limited to these specific examples alone.

EXAMPLE 1

Synthesis of an intermediate of general formula (II):
12.3 g of 2-amino-4,6-dimethylpyrimidine was suspended in 300 ml of dimethylformamide, and 4 g of sodium hydroxide (oily 60%) was added. The mixture was stirred at room temperature for 1 hour. Furthermore, 33.7 g of dimethyl N-(2-biphenylylsulfonyl)carbonimidodithioate was added, and the mixture was stirred at room temperature for a day and night. The reaction mixture was poured into 2 liters of water, and filtered. When the filtrate was made weakly acidic, white crystals precipitated. The crystals were collected by filtration, and recrystallized from ethanol to give 29.2 g of the desired 1-(2-biphenylylsulfonyl)3-(4,6-dimethylpyrimidin-2-yl)2-methylisothiourea of the following formula, mp. 154°–157° C.:

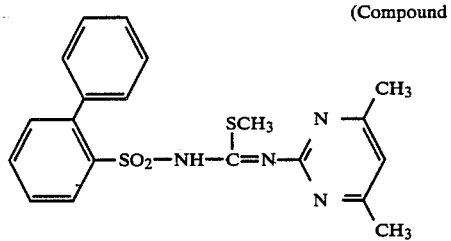

(Compound No. II-1)

By substantially the same method as in Example 1, the following compounds were synthesized:
Compound No. II-2: 1-(2-biphenylylsulfonyl)3-(4-methoxy-6-methylpyrimidin-2-yl)2-methylisothiourea. mp. 138°–140° C.
Compound No. II-3: 3-(4,6-dimethylpyrimidin-2-yl)2-methyl-1-(2-phenoxyphenylsulfonyl)isothiourea. mp. 143°–145° C.

The following example shows the synthesis of dimethyl N-(2-biphenylylsulfonyl)carbonimidodithioate used in Example 1:

EXAMPLE 2

116.5 g of 2-phenylbenzenesulfonamide was dissolved in 500 ml of dimethylformamide, and 38 g of carbon disulfide and 28 g of potassium hydroxide were added to the solution, and the mixture was stirred at room temperature for 7 hours. To the reaction mixture was added 28 g of potassium hydroxide, and the mixture was stirred at room temperature for 2 hours. When 400 ml of ethyl acetate was added dropwise, a pale yellow precipitate formed. The crystals were collected by filtration, and washed with ethyl acetate. The resulting potassium N-(2-biphenylylsulfonyl)carbonimidodithioate was dissolved in 400 ml of dimethylformamide, and 126 g of dimethyl sulfate was added dropwise to the solution at 60° C. over the course of 1 hour. After the addition, the mixture was heated at 80° C. for 2 hours. After cooling, the reaction mixture was poured into 1 liter of water, and the precipitated crystals were collected by filtration. There was obtained 270 g of the desired dimethyl N-(2-biphenylylsulfonyl)carbonimidodithioate of the following formula, mp. 115°–117° C.:

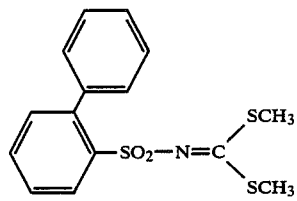

(Compound No. IV-1)

By substantially the same method, dimethyl N-(2-phenoxyphenylsulfonyl)carbonimidodithioate (compound No. IV-2) was synthesized.

EXAMPLE 3

Synthesis of an intermediate of general formula (II):
3.98 g of 1-(2-biphenylylsulfonyl)3-(4,6-dimethylpyrimidin-2-yl)thiourea was suspended in 50 ml of dry acetonitrile, and a solution of 0.3 g of metallic sodium in 10 ml of ethanol was added, and the mixture was heated under reflux for 30 minutes. After cooling, 1.85 g of methyl iodide was added, and the mixture was heated under reflux for 5 hours. The reaction mixture was cooled, and then poured into 100 ml of water. The product was extracted with methylene chloride. Methylene chloride was evaporated under reduced pressure, and the residue was recrystallized from ethanol to give 1.6 g of the desired 1-(2-biphenylylsulfonyl)3-(4,6-dimethylpyrimidin-2-yl)2-methylisothiourea (compound No. II-1) which was the same as obtained in Example 1. mp. 154°–157° C.

An example of the synthesis of 1-(2-biphenylylsulfonyl)3-(4,6-dimethylpyrimidin-2-yl)thiourea used in Example 3 is shown below.

EXAMPLE 4

Synthesis of an intermediate of general formula (VI):
77 g of potassium N-(2-biphenylylsulfonyl)carbonimidodithioate prepared in accordance with Example 2 was suspended in 100 ml of toluene, and 37 ml of thionyl chloride was added to the suspension at 0° to 10° C. over the course of 1 hour. After the addition, the mixture was stirred at room temperature for 2 hours. The reaction mixture was filtered, and the filtrate was concentrated under reduced pressure. Distillation at reduced pressure gave 2-phenylbenzenesulfonyl isothiocyanate. On the other hand, 12.3 g of 2-amino-4,6-dimethylpyrimidine was suspended in 300 ml of dry toluene, and 27.5 g of 2-phenylbenzenesulfonyl isothiocyanate prepared as above was added. The mixture was heated under reduced pressure for 8 hours. After cooling, the resulting white precipitate was collected by filtration, and recrystallized from ethanol to give 31 g of the desired 1-(2-biphenylsulfonyl)3-(4,6-dimethylpyrimidin-2-yl)thiourea of the following formula, mp. 203°–204° C.:

(Compound No. VI-1)

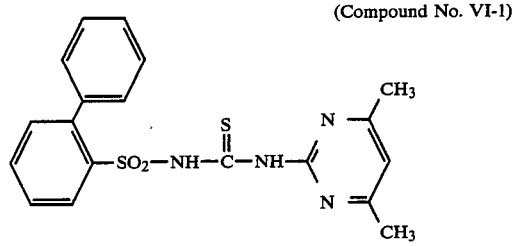

By substantially the same method as in Example 4, the following compounds were synthesized:

Compound No. VI-2: 1-(2-biphenylylsulfonyl)3-(4-methoxy-6-methylpyrimidin-2-yl)thiourea. mp. 203°–204° C.

Compound No. VI-3: 3-(4,6-dimethylpyrimidin-2-yl)1-(2-phenoxyphenylsulfonyl)thiourea

EXAMPLE 5

Synthesis of the final compound of general formula (I):

4.12 g of 1-(2-biphenylsulfonyl)3-(4,6-dimethylpyrimidin-2-yl)2-methylisothiourea was dissolved in 50 ml of dioxane, 2.35 g of O-methylhydroxylamine was added to the solution, and the mixture was heated under reflux for 5 hours. After cooling the reaction mixture, the solvent was evaporated under reduced pressure. The residue was recrystallized from ethanol to give 2.6 g of the desired N-(2-biphenylsulfonyl)N'-(4,6-dimethylpyrimidin-2-yl)N''-(methoxy)guanidine of the following formula, mp. 190°–192° C.:

(Compound No. I-1)

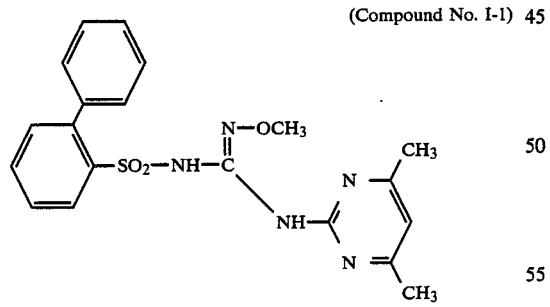

By substantially the same method as in Example 5, the following compounds were synthesized:

Compound No. I-2: N-(2-biphenylylsulfonyl)N'-(4-methoxy-6-methylpyrimidin-2-yl)N''-(methoxy)-guanidine. mp. 140°–141° C.

Compound No. I-3: N-(2-phenoxyphenylsulfonyl)N'-(4,6-dimethylpyrimidin-2-yl)N''-(methoxy)guanidine. mp. 139°–142° C.

Compound No. I-4: N-(2-biphenylylsulfonyl)N'-(4-methoxy-6-methylpyrimidin-2-yl)N''-(propoxy)-guanidine.

Compound No. I-5: N-(2-biphenylylsulfonyl)N'-(4-methoxy-6-methylpyrimidin-2-yl)N''-(methyl)-guanidine.

Compound No. I-6: N-(2-biphenylylsulfonyl)N'-(4-methoxy-6-methylpyrimidin-2-yl)guanidine.

EXAMPLE 5

Wettable powder:

Fifteen parts of compound No. I-1 of the invention, 80 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and dropped onto weeds and/or their habitat.

EXAMPLE 6

Emulsifiable concentrate:

Thirty parts of compound No. I-1 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and dropped onto weeds and/or their habitat.

EXAMPLE 7

Dust:

Compound No. I-3 of the invention (2 parts) and 98 parts of powdery clay are pulverized and mixed to form a dust. It is scattered over weeds and/or their habitat.

EXAMPLE 8

Dust:

Compound No. I-4 of the invention (1.5 parts), 0.5 part of isopropyl hydrogen phosphate (PAP) and 98 parts of powdery clay are pulverized and mixed to form a dust. It is scattered over weeds and/or their habitat.

EXAMPLE 9

Granules:

Water (25 parts) is added to a mixture consisting of 10 parts of compound No. I-2 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over weeds and/or their habitat.

EXAMPLE 10

Granules:

Ninety-five parts of clay mineral particles having a particle size distribution between 0.2 and 2 mm are put in a rotary mixer, and with rotation, 5 parts of compound No. I-5 of the invention dissolved in an organic solvent is sprayed onto the clay mineral particles to wet them uniformly. The particles are then dried at 40° to 50° C. to form granules. They are scattered over weeds and/or their habitat.

EXAMPLE 11

Test of stalk-foliar/soil treatment of aquatic paddy weeds in the watered state (pot test):

Preparation of an active compound:

Carrier: 5 parts by weight of acetone
Emulsifier: 1 part by weight of benzyloxypolyglycol ether A preparation containing the active compound is formed by mixing 1 part by weight of each of the active compounds with the carrier and emulsifier in the amounts shown above, and diluting a predetermined amount of the resulting emulsifiable concentrate with water.

Testing method:

Aquatic paddy soil was filled in Wagner pots (1/5,000 ares), and rice seedlings (variety: Kinnampu) in the 2- to 3-leaf stage (plant height about 10 cm) were transplanted at a rate of 2 per pot. Seeds of *Monochoria vaginalis, Scirpus juncoides* and broad-leaved weeds, small fragments of *Eleocharis acicularis*, and tubers of *Cyperus serotinus* and *Sagittaria pygmaea* were inoculated in the pots. The soil in the pots was maintained in the wet state. About 7 to 9 days after sowing, each pot was watered to a depth of about 6 cm. A predetermined amount of the compound of this invention in the form of an emulsion was applied by a pipette to treat each pot. After the treatment, the pots were watered for 2 days at a rate of 2 to 3 cm per day while allowing leakage, and thereafter maintained in the watered state to a depth of about 3 cm. In the fourth week after treatment by the chemical, the weed control effect and the degree of phytotoxicty were evaluated on a scale of 0 to 5 as follows:

Evaluation of the weed control effect (the herbicidal rate based on the non-treated area):
5: at least 95% (withered)
4: at least 80% but less than 95%
3: at least 50% but less than 80%
2: at least 30% but less than 50%
1: at least 10% but less than 30%
0: less than 10% (no effect)

Evaluation of phytotoxicity to rice (the phytotoxicity rate based on the non-treated area):
5: at least 90% (fatal injury)
4: at least 50% but less than 90%
3: at least 30% but less than 50%
2: at least 10% but less than 30%
1: more than 0% but less than 10%
0: 0% (no phytotoxicity)

The results are shown in Table 1.

TABLE 1

| Compound No. | Amount of the active ingredient (kg/ha) | Weed control effect Weeds | | | | | | Phytotoxicity Rice |
|---|---|---|---|---|---|---|---|---|
| | | A | B | C | D | E | F | |
| I - 1 | 0.5 | 5 | 5 | 5 | 5 | 4 | 5 | 0 |
| I - 2 | 0.5 | 5 | 5 | 5 | 5 | 4 | 5 | 0 |
| I - 3 | 0.5 | 5 | 5 | 5 | 5 | 4 | 5 | 0 |
| I - 4 | 0.5 | 5 | 5 | 5 | 5 | 4 | 5 | 0 |
| I - 5 | 0.5 | 5 | 5 | 5 | 5 | 4 | 5 | 0 |
| Comparison simetryn | 0.5 | 4 | 3 | 5 | 5 | 2 | 2 | 2 |

Note:
1. The compound numbers correspond to those given hereinabove.
2. The symbols A, B, C, D, E and F in the column of Weeds represent the following weeds.
A: *Eleocharis acicularis*
B: *Scirpus juncoides*
C: *Monochoria vaginalis*
D: Broad-leaved weeds (*Lindernia procumbens, Rotala indica, Elatine triandra*, etc.)
E: *Cyprus serotinus*
F: *Sagittaria pygmaea*
3. Comparison, simetryn (common name): 2,4-bis(ethylamino)-6-methylthio-1,3,5-triazine By the same testing method as in Example 11, the weed control effects of the compounds of general formulae (II) and (VI) which are novel intermediates of the invention were tested. The results are shown in Table 2.

TABLE 2

| Compound No. | Amount of the effective ingredient (kg/ha) | Weed control effect Weed | | | | | | Phytotoxicity Rice |
|---|---|---|---|---|---|---|---|---|
| | | A | B | C | D | E | F | |
| II - 1 | 0.5 | 5 | 5 | 5 | 5 | 4 | 5 | 0 |
| VI - 1 | 0.5 | 5 | 5 | 5 | 5 | 4 | 5 | 0 |

Note:
1. The compound numbers are the same as those given hereinabove
2. The symbols in the column of Weeds are the same as in Table 1.

It will be appreciated that the instant specification and examples are set forth by way of illustration and not limitation, and that various modifications and changes may be made without departing from the spirit and scope of the present invention.

What is claimed is:

1. A substituted phenylsulfonyl guanidine of the formula

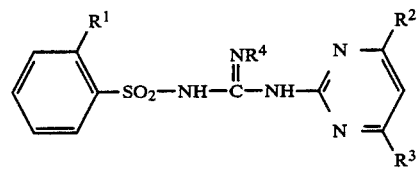

in which
$R^1$ is a phenyl or phenoxy group,
$R^2$ and $R^3$ each independently is a lower alkyl or lower alkoxy group, and
$R^4$ is a hydrogen atom, a lower alkyl group or a lower alkoxy group.

2. A compound according to claim 1, wherein such compound is N-(2-biphenylylsulfonyl)N'-(4-methoxy-6-methylpyrimidin-2-yl)N''-(methoxy)guanidine of the formula

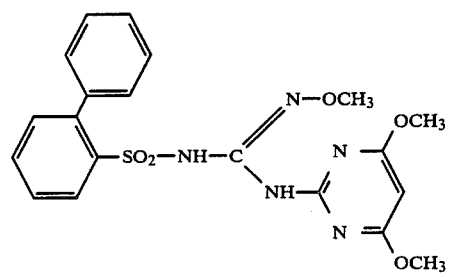

3. A compound according to claim 1, wherein such compound is N-(2-biphenylsulfonyl)N'-(4,6-dimethylpyrimidin-2-yl)N''-(methoxy)guanidine of the formula

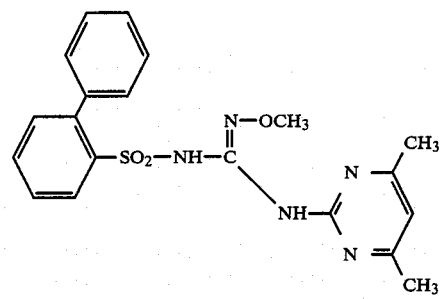

4. A compound according to claim 1, wherein such compound is N-(2-phenoxyphenylsulfonyl)N'-(4,6-dimethylpyrimidin-2-yl)N''-(methoxy)guanidine of the formula

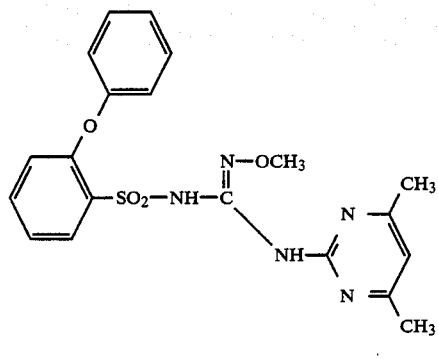

5. A compound according to claim 1, wherein such compound is N-(2-biphenylylsulfonyl)N'-(4-methoxy-6-methylpyrimidin-2-yl)N''-(propoxy)guanidine of the formula

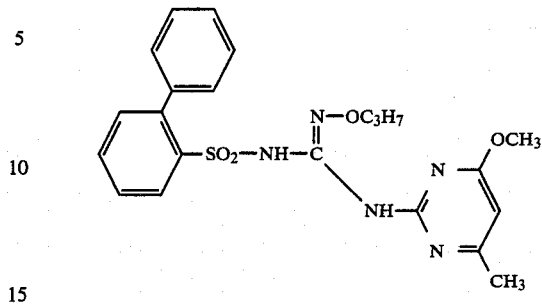

6. A compound according to claim 1, wherein such compound is N-(2-biphenylylsulfonyl)N'-(4-methoxy-6-methylpyrimidin-2-yl)N'''(methyl)guanidine of the formula

7. A compound according to claim 1, wherein such compound is N-(2-biphenylylsulfonyl)N'-(4-methoxy-6-methylpyrimidin-2-yl)-guanidine of the formula

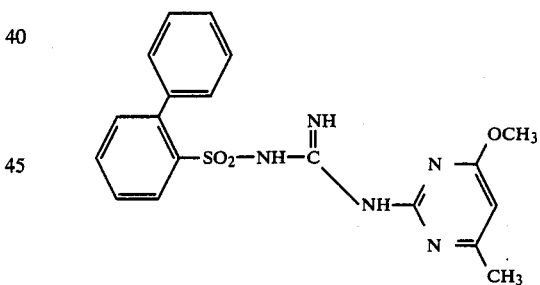

8. A herbicidal composition comprising a herbicidally effective amount of a substituted phenylsulfonyl guanidine derivative according to claim 1 in admixture with a diluent.

9. A method of killing unwanted vegetation which comprises applying to such vegetation or to a field in which said vegetation might grow a herbicidally effective amount of a compound according to claim 1.

* * * * *

UNITED STATES PATENT AND TRADEMARK OFFICE
CERTIFICATE OF CORRECTION

PATENT NO. : 4,559,079

DATED : December 17, 1985

INVENTOR(S) : Kozo Shiokawa, et al.

It is certified that error appears in the above-identified patent and that said Letters Patent is hereby corrected as shown below:

Col. 16, line 64   End of formula delete " 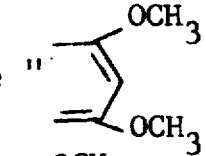 "

and substitute -- 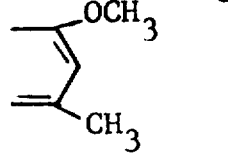 --

Signed and Sealed this

Twenty-second Day of July 1986

[SEAL]

Attest:

DONALD J. QUIGG

Attesting Officer

Commissioner of Patents and Trademarks